US009433344B2

(12) United States Patent
Avitsian et al.

(10) Patent No.: US 9,433,344 B2
(45) Date of Patent: *Sep. 6, 2016

(54) ENDOSCOPIC SHEATH ASSEMBLY

(71) Applicant: THE CLEVELAND CLINIC FOUNDATION, Cleveland, OH (US)

(72) Inventors: Rafi Avitsian, Solon, OH (US); Andrew M. Zura, Broadvies Hts., OH (US); Robert B. Guthrie, Ventura, CA (US); Douglas W. Haight, Camarillo, CA (US); James T. Callegari, Ventura, CA (US); Michael Collinson, Camarillo, CA (US)

(73) Assignee: The Cleveland Clinic Foundation, Cleveland, OH (US)

( * ) Notice: Subject to any disclaimer, the term of this patent is extended or adjusted under 35 U.S.C. 154(b) by 93 days.

This patent is subject to a terminal disclaimer.

(21) Appl. No.: 14/450,562

(22) Filed: Aug. 4, 2014

(65) Prior Publication Data

US 2014/0357955 A1    Dec. 4, 2014

Related U.S. Application Data

(63) Continuation of application No. 13/273,918, filed on Oct. 14, 2011, now Pat. No. 8,814,781.

(51) Int. Cl.
*A61B 1/00* (2006.01)
*A61B 1/12* (2006.01)
(Continued)

(52) U.S. Cl.
CPC ............ *A61B 1/126* (2013.01); *A61B 1/00064* (2013.01);
(Continued)

(58) Field of Classification Search
CPC .......... A61B 1/00062; A61B 1/00057; A61B 1/00135; A61B 1/00142; A61B 1/00089; A61B 1/00101; A61B 1/00094
USPC ........ 600/104, 114, 121, 127–129, 153–159, 600/207, 208; 604/538, 539
See application file for complete search history.

(56) References Cited

U.S. PATENT DOCUMENTS 4,132,227 A    1/1979   Ibe
4,406,656 A    9/1983   Hattler et al.
(Continued)

FOREIGN PATENT DOCUMENTS

WO    2010111461 A1    9/2010

OTHER PUBLICATIONS

PCT International Search Report and Written Opinion for PCT/US2011/056384, mailed Jun. 27, 2012, pp. 1-25.

*Primary Examiner* — Anhtuan T Nguyen
*Assistant Examiner* — Timothy J Neal
(74) *Attorney, Agent, or Firm* — Tarolli, Sundheim, Covell & Tummino LLP

(57) ABSTRACT

A sheath assembly for an endoscope includes an elongate tubular body and a plug. The endoscope has a handle portion and a scope portion extending therefrom to a tip. The body includes first and second wall sections and extends along a longitudinal axis between first and second distal openings. The first wall section extends radially about the longitudinal axis to define a scope lumen. The scope portion is receivable in the scope lumen. The second wall section extends radially about a portion of the first wall section and longitudinally between second distal and proximal end openings. The first and second wall sections define an integral suction lumen in fluid communication with a first source of negative pressure. The plug is mated with the distal end opening for closing the scope lumen and includes at least one suction opening disposed in co-registration with the first distal end opening.

14 Claims, 9 Drawing Sheets

(51) Int. Cl.
 *A61B 1/015* (2006.01)
 *A61B 1/04* (2006.01)

(52) U.S. Cl.
 CPC ....... *A61B 1/00066* (2013.01); *A61B1/00094* (2013.01); *A61B 1/00126* (2013.01); *A61B 1/00128* (2013.01); *A61B 1/00135* (2013.01); *A61B 1/00137* (2013.01); *A61B 1/00142* (2013.01); *A61B 1/015* (2013.01); *A61B 1/00101* (2013.01)

(56) References Cited

U.S. PATENT DOCUMENTS

| | | |
|---|---|---|
| 5,738,630 A | 4/1998 | Suzuki et al. |
| 6,997,867 B2 | 2/2006 | Soble et al. |
| 7,056,284 B2 | 6/2006 | Martone et al. |
| 7,120,354 B2 | 10/2006 | Mackie et al. |
| 7,811,228 B2 | 10/2010 | Adams |
| 2003/0176769 A1 | 9/2003 | Soble et al. |
| 2004/0010183 A1 | 1/2004 | Dhindsa |
| 2006/0020165 A1 | 1/2006 | Adams |
| 2006/0269442 A1 | 11/2006 | Nguyen |

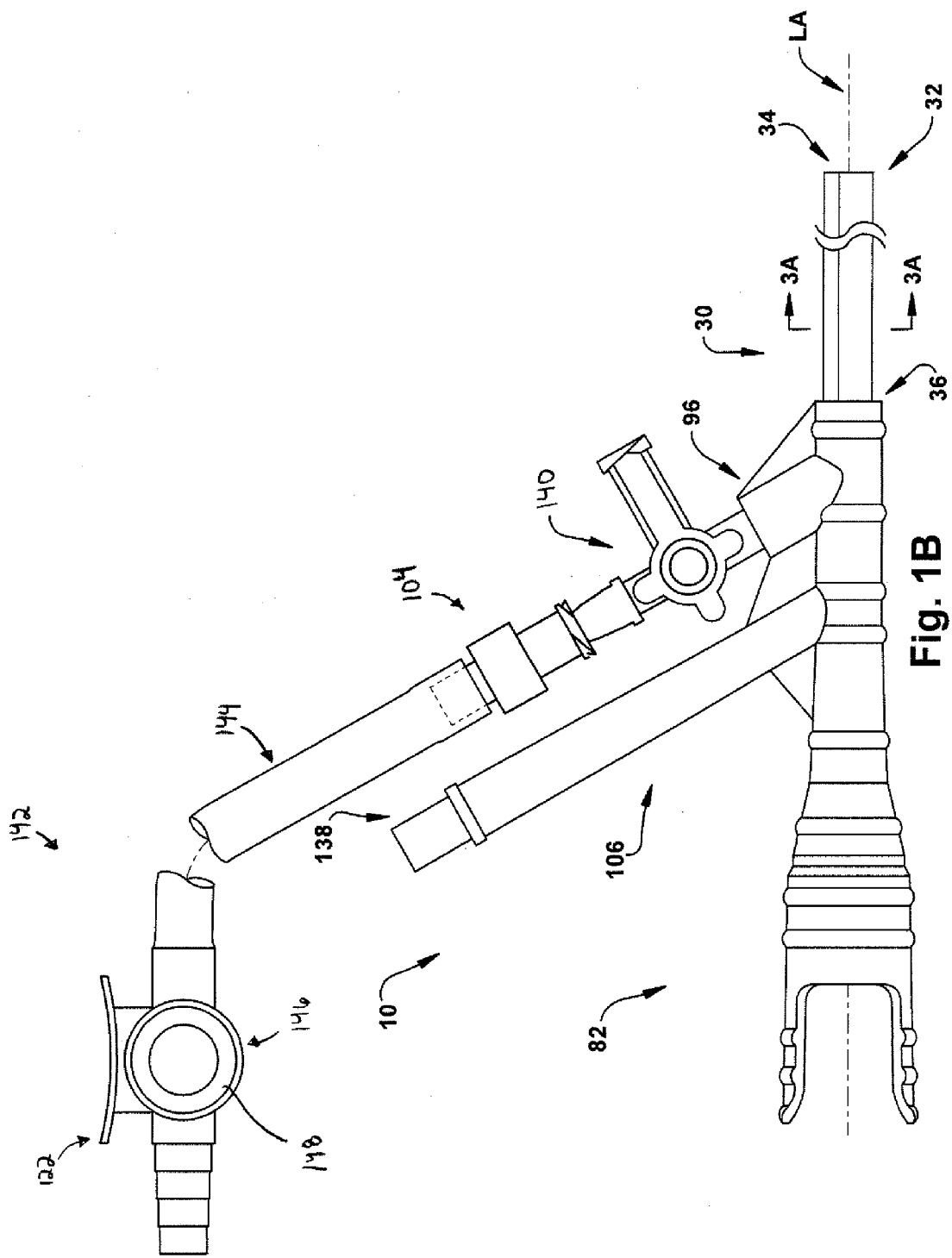

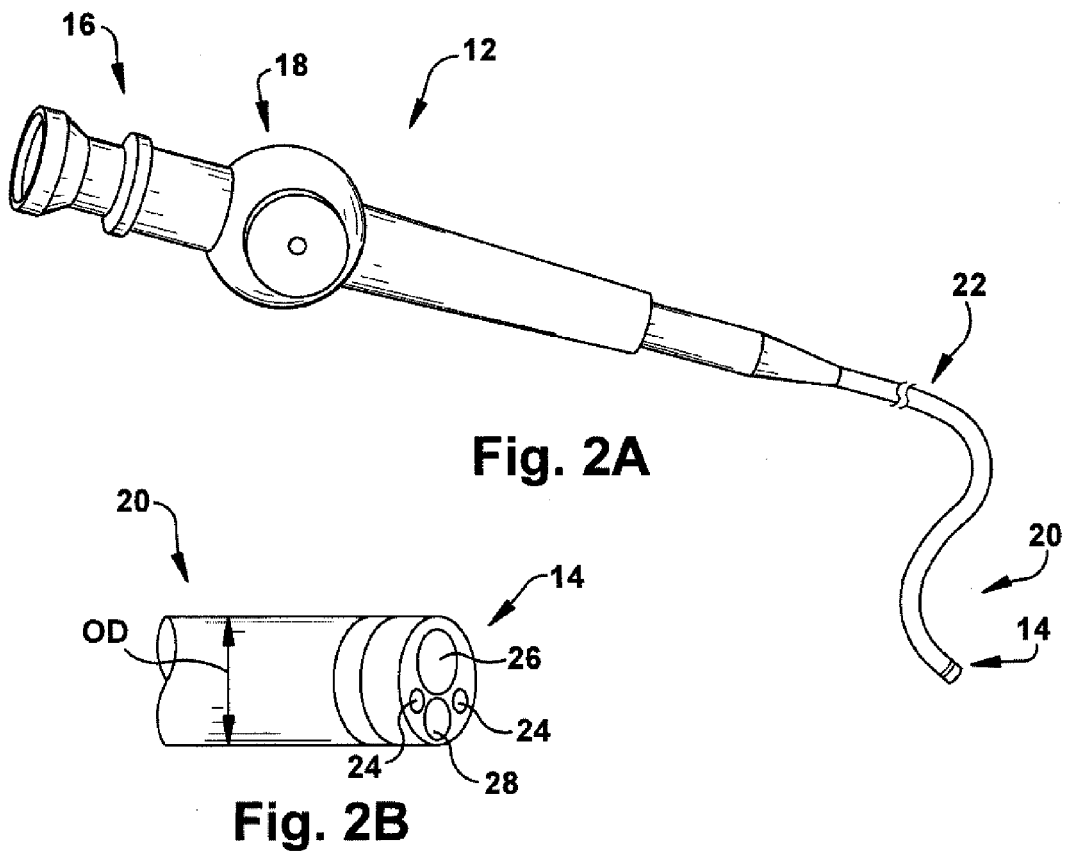
Fig. 2A
Fig. 2B
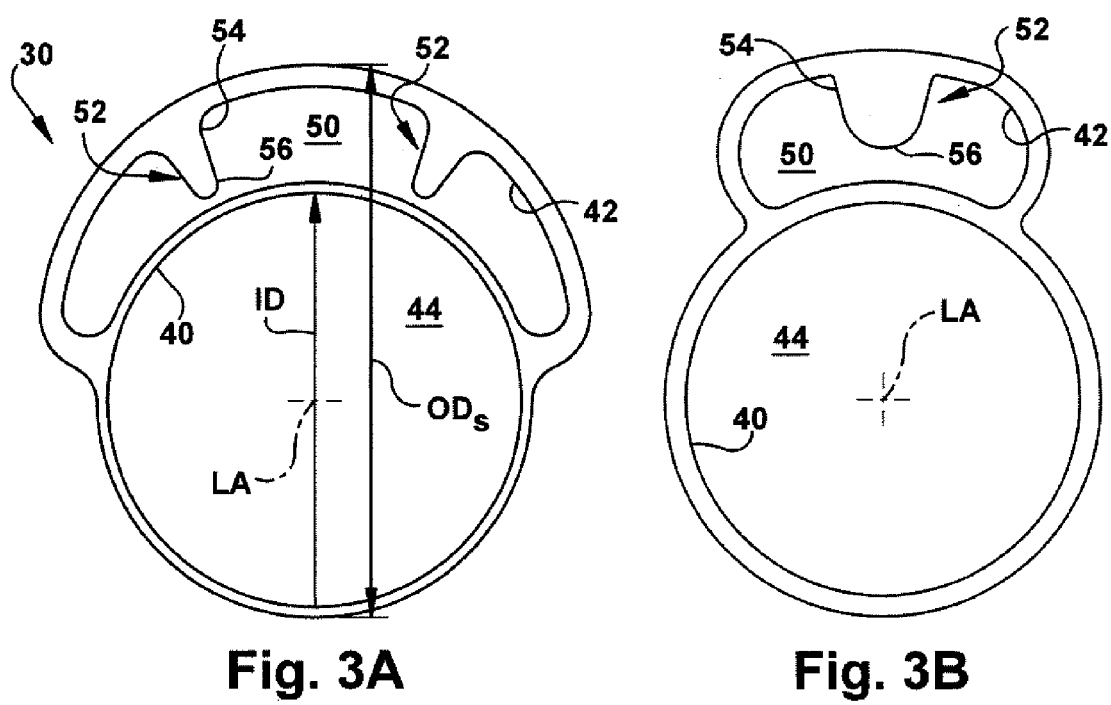
Fig. 3A
Fig. 3B

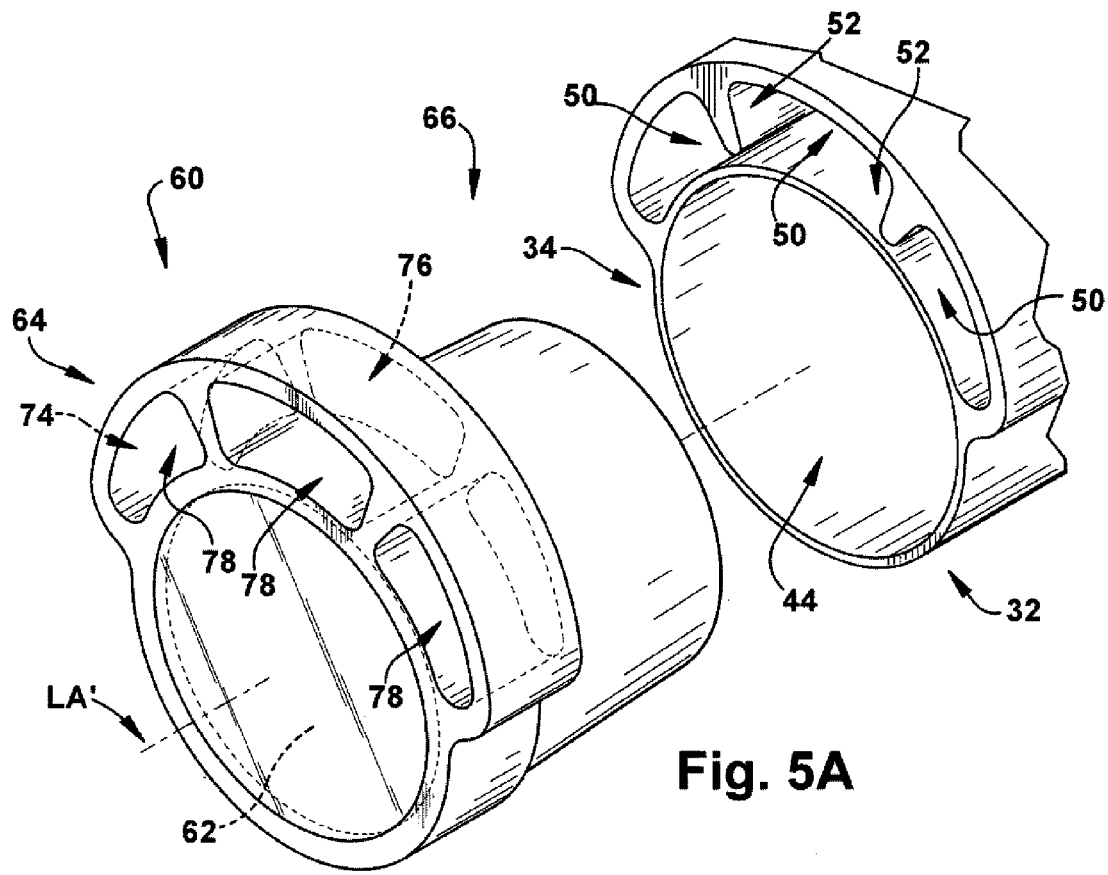
Fig. 5A
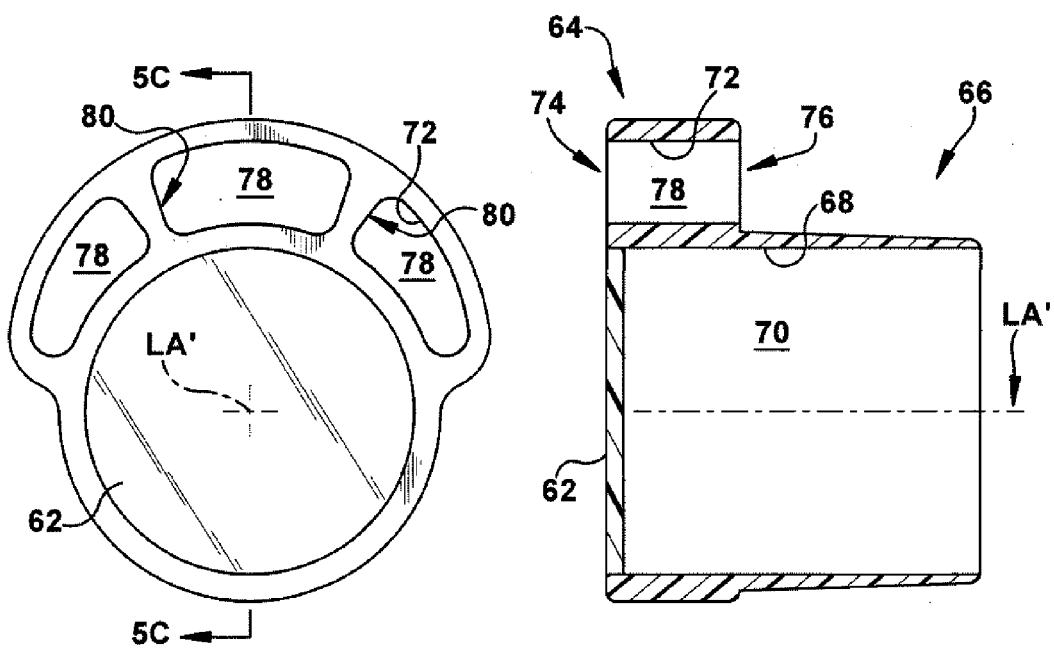
Fig. 5B  Fig. 5C

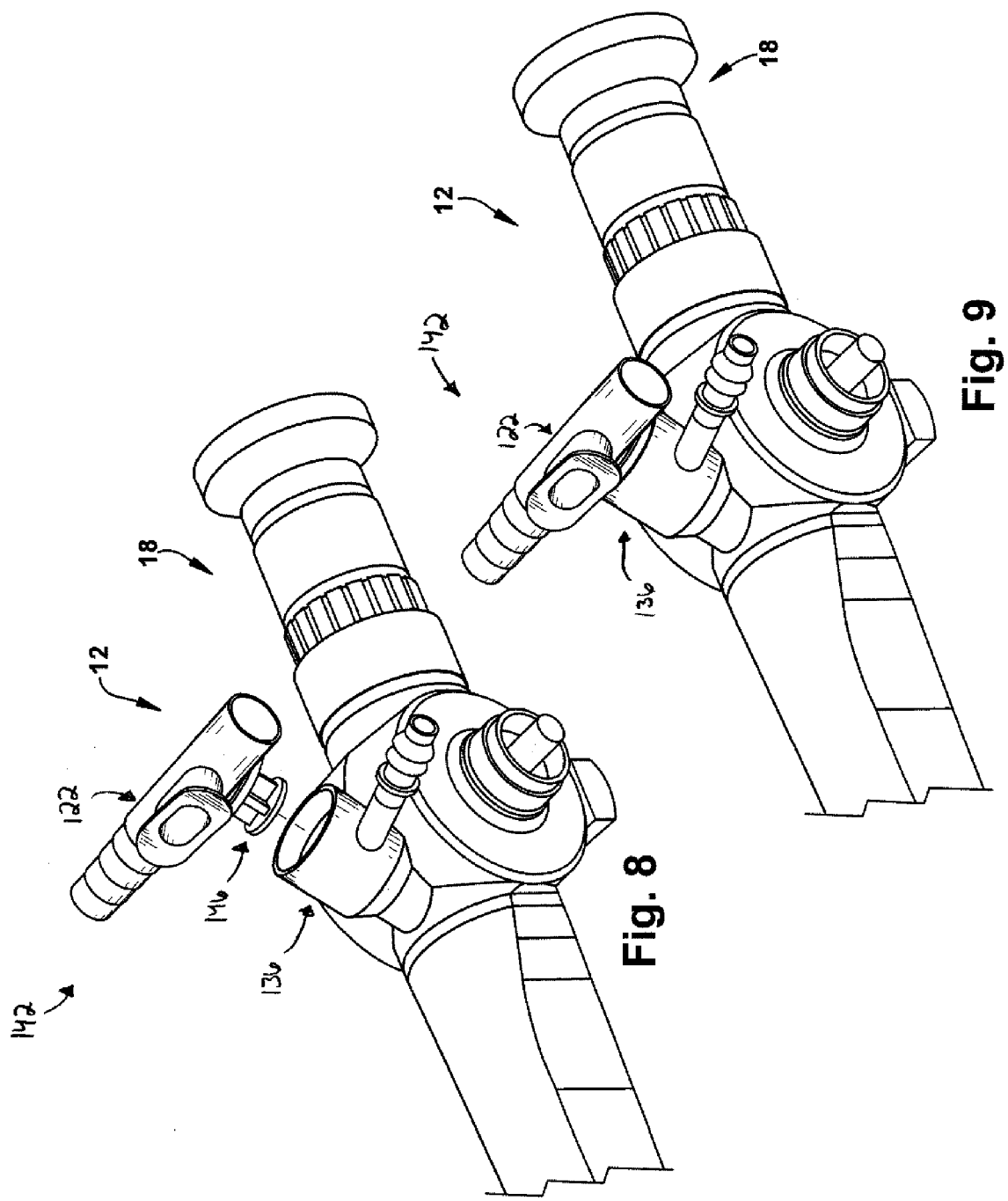

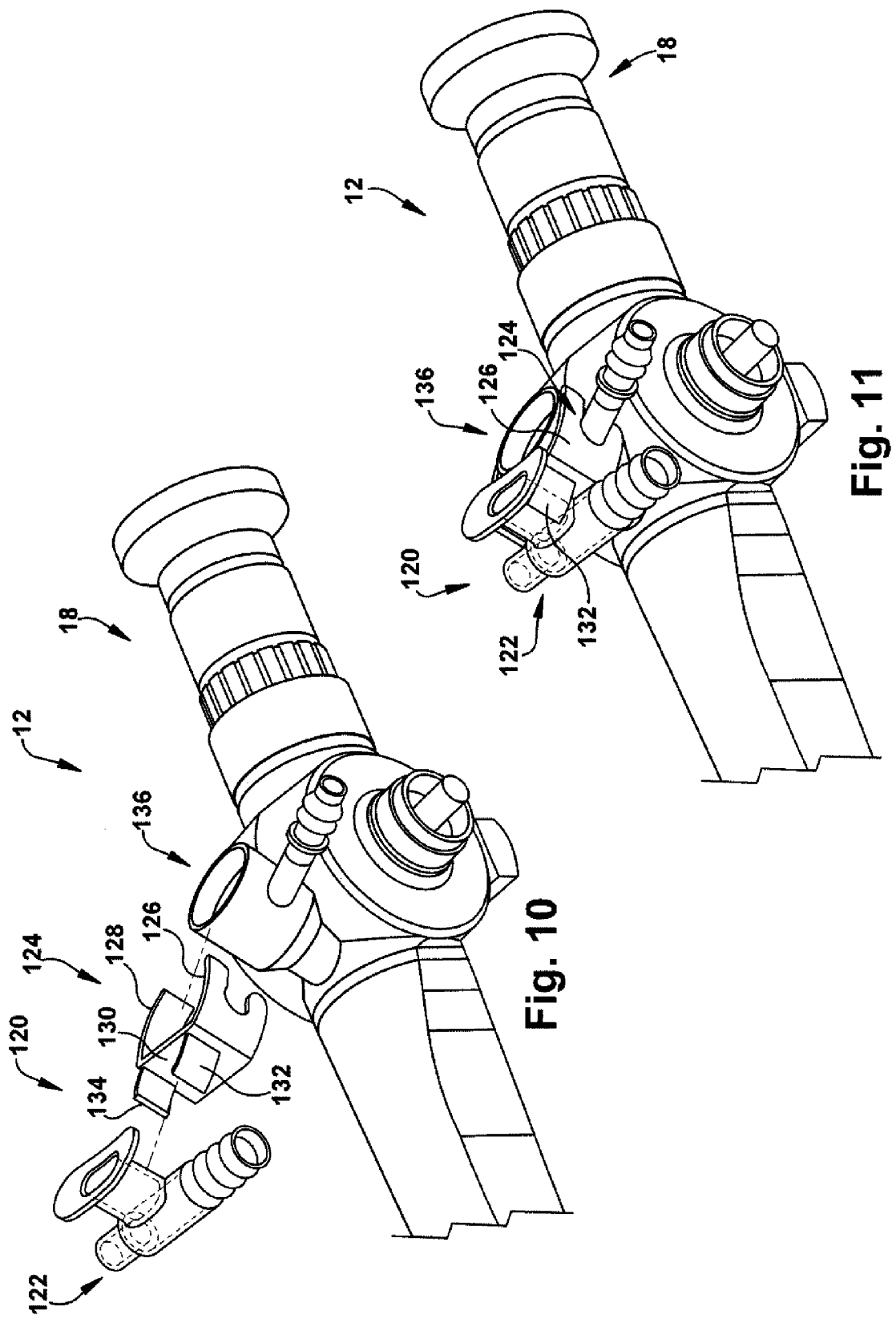

ENDOSCOPIC SHEATH ASSEMBLY

RELATED APPLICATIONS

This application is a continuation of U.S. patent application Ser. No. 13/273,918, filed Oct. 14, 2011, which is a continuation-in-part of U.S. patent application Ser. No. 13/257,529, filed Sep. 19, 2011, which is a U.S. National Stage application of PCT Appln. No. PCT/US2010/028614, filed Mar. 25, 2010, which claims the benefit of U.S. Provisional Patent Appln. Ser. No. 61/163,171, filed Mar. 25, 2009. This application claims the benefit of all of the above-identified applications, as well as U.S. Provisional Patent Appln. Ser. No. 61/393,207, filed Oct. 14, 2010. All of the above-identified applications are incorporated herein by reference in their entireties for all purposes.

TECHNICAL FIELD

The present invention generally relates to a sheath for medical devices, and more particularly to a sheath assembly having at least one internal suction lumen for invasive medical devices, such as endoscopes and bronchoscopes.

BACKGROUND OF THE INVENTION

Endoscopes are routinely used in medical procedures to allow internal visualization. Many of these endoscopes have an integral suction lumen, which may be used, among other things, to aspirate bodily fluids and/or foreign bodies. It is normal clinical practice to clean and sterilize these generally very expensive scopes between patients. The cleaning process is costly due to degradation of the scope during cleaning and the requirement for additional scopes to ensure availability while others are being reprocessed.

The use of a disposable sheath to protect the scope from contamination during use is well known. However, placing this sheath over the scope disables the ability of the user to utilize the scope's integral suction lumen. It is possible to design the sheath so that it incorporates one or more additional lumens through which suction can be drawn. There is currently at least one disposable sheath product on the market that provides such alternate suction capability. It is desirable that a sheath-specific suction lumen (or lumens) afford a cross-sectional area as large as possible (e.g., at least as large as the one integral to the scope). If multiple suction lumens are provided, it is also desirable that the cross-sectional area of any one of these be reasonably large so as to minimize the potential for occlusion.

Many endoscopes incorporate an articulating distal section that is controlled proximally by the user. It is important that a sheath does not appreciably impair the ability of the scope during articulation. Examples of endoscopes and endoscope sheaths are described in PCT Publication No. WO 2010/111461, U.S. Pat. No. 7,056,284, and U.S. Pat. No. 7,120,354, the entireties of which are hereby incorporated by reference.

SUMMARY OF THE INVENTION

One aspect of the present invention includes a sheath assembly for an endo scope. The endoscope has a handle portion and an elongate scope portion extending from the handle portion to a tip. The sheath assembly comprises an elongate tubular body and a plug. The elongate tubular body comprises a first wall section and a second wall section. The elongate tubular body extends along a longitudinal axis between a first distal opening located at a distal end thereof, and a first proximal end opening located at a proximal end thereof. The first wall section extends radially about the longitudinal axis to define a scope lumen. The scope portion of the endoscope is receivable coaxially in the scope lumen with the distal end of the body being disposed adjacent the endoscope tip, and the proximal end of the body is disposed adjacent the handle portion of the endoscope. The second wall section extends radially about at least a portion of the first wall section and longitudinally along the longitudinal axis between a second distal opening adjacent the first distal end opening and second proximal end opening adjacent the first proximal end opening. The first and second wall sections define an integral suction lumen therebetween connectable in fluid communication with a first source of negative pressure. The plug is mated with the distal end opening of the body for closing the scope lumen. The plug has a lens surface through which light or other energy is transmissible to or from the endoscope tip.

Another aspect of the present invention includes a sheath assembly for an endoscope. The endoscope has a handle portion and an elongate scope portion extending from the handle portion to a tip. The sheath assembly comprises an elongate tubular body, a plug and a connector. The elongate tubular body comprises a first wall section and a second wall section. The elongate tubular body extends along a longitudinal axis between a first distal opening located at a distal end thereof, and a first proximal end opening located at a proximal end thereof. The first wall section extends radially about the longitudinal axis to define a scope lumen. The scope portion of the endo scope is receivable coaxially in the scope lumen with the distal end of the body being disposed adjacent the endoscope tip, and the proximal end of the body is disposed adjacent the handle portion of the endoscope. The second wall section extends radially about at least a portion of the first wall section and longitudinally along the longitudinal axis between a second distal opening adjacent the first distal end opening and second proximal end opening adjacent the first proximal end opening. The first and second wall sections define an integral suction lumen therebetween connectable in fluid communication with a first source of negative pressure. The plug is mated with the distal end opening of the body for closing the scope lumen. The plug has a lens surface through which light or other energy is transmissible to or from the endoscope tip. The connector extends longitudinally between a forward end portion that coaxially surrounds the first and second proximal end openings, and a rearward end portion configured to fit onto the handle portion of the endoscope.

Another aspect of the present invention includes a method for detecting a leak in a sheath assembly. One step of the method includes providing a sheath assembly. The sheath assembly comprises an elongate tubular body and a plug. The elongate tubular body comprises a first wall section and a second wall section. The elongate tubular body extends along a longitudinal axis between a first distal opening located at a distal end thereof, and a first proximal end opening located at a proximal end thereof. The first wall section extends radially about the longitudinal axis to define a scope lumen. The second wall section extends radially about at least a portion of the first wall section and longitudinally along the longitudinal axis between a second distal opening adjacent the first distal end opening and second proximal end opening adjacent the first proximal end opening. The first and second wall sections define an integral suction lumen therebetween connectable in fluid communication with a first source of negative pressure. The plug is mated with the distal end opening of the body for closing the scope lumen. The plug has a lens surface through which light or other energy is transmissible to or from the endoscope tip. Next, a portion of the body is inserted into a fluid-filled container. The container is then monitored for the presence of at least one bubble emanating from the portion of the body. The presence of at least one bubble indicates a leak in the portion of the body.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1B is a side view of the sheath assembly shown in FIG. 1A;

FIG. 2A is a schematic illustration showing a perspective view of an endoscope;

FIG. 2B is a schematic illustration showing a magnified perspective view of a distal tip of the endoscope in FIG. 2A;

FIG. 3A is a cross-sectional view of a distal end of the sheath assembly taken along Line 3A-3A in FIG. 1B;

FIG. 3B is a cross-sectional view showing an alternative configuration of the distal end in FIG. 3A;

FIG. 5A is a schematic illustration showing a perspective view of a plug comprising the sheath assembly in FIGS. 1A-B;

FIG. 5B is a schematic illustration showing a front side view of the plug in FIG. 5A;

FIG. 5C is a schematic illustration showing a side view of the plug in FIG. 5A;

FIG. 8 is a schematic illustration showing a perspective view of a plug assembly (exploded);

FIG. 9 is a schematic illustration showing a perspective view of the plug assembly in FIG. 8 mated with an integral valve port of the endoscope;

FIG. 10 is a schematic illustration showing a perspective view of a clip and valve assembly (exploded); and FIG. 11 is a schematic illustration showing a perspective view of the clip and valve assembly in FIG. 10 mated with a handle portion of the endoscope.

DETAILED DESCRIPTION

Figure 1A:
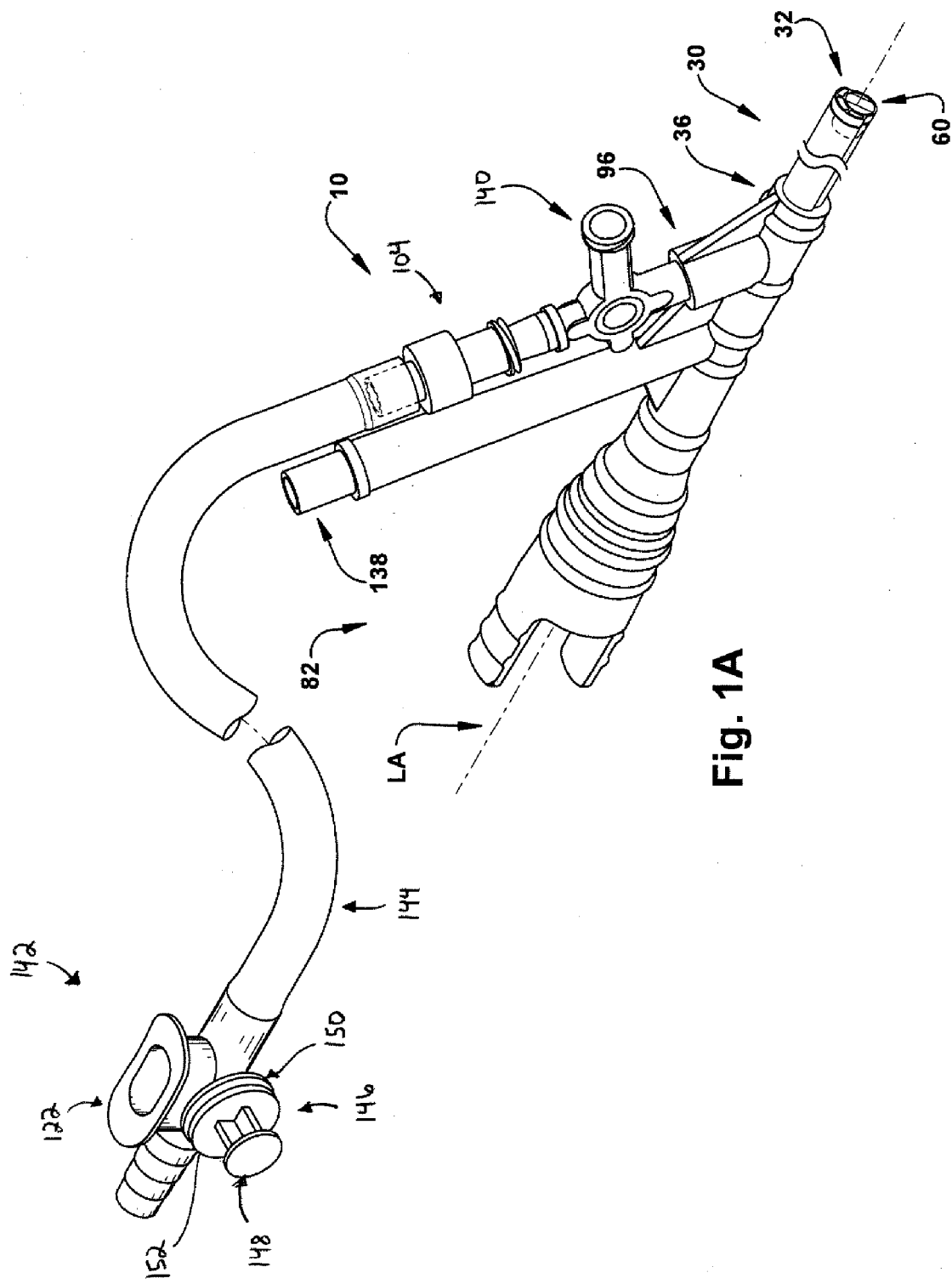
FIG. 1A is a schematic illustration showing a perspective view of a sheath assembly constructed in accordance with one aspect of the present invention.

The present invention generally relates to a sheath for medical devices, and more particularly to a sheath assembly having at least one internal suction lumen for invasive medical devices, such as endoscopes and bronchoscopes. As representative of one aspect of the present invention, FIGS. 1A-B illustrate a sheath assembly 10 for an endoscope 12 (FIGS. 2A-B). As described in more detail below, the sheath assembly 10 (FIGS. 1A-B) of the present invention advantageously: (1) protects endoscopes 12 from contamination while still allowing suctioning; (2) is useful with standard endoscopes (i.e., having round cross-sectional profiles); (3) provides suction around a greater portion of the distal endoscope tip 14 (FIGS. 2A-B); and (4) includes a leak detection mechanism for evaluating the integrity of the sheath assembly before and/or after use.

Generally speaking, endoscopes 12 contain an internal suction lumen (not shown) to provide a pathway for suctioning a patient. One example of an endoscope 12 is shown in FIGS. 2A-B and includes a proximal end portion 16 having a handle portion 18 connected thereto, a distal end portion 20 having a distal tip 14, and an elongate scope portion 22 that extends between the proximal and distal end portions. The endoscope 12 can be equipped with an illumination device 24, a viewing device 26, and a working lumen or channel 28. The illumination device 24 can provide light for the operation of the endoscope 12 in a dark bodily lumen. The viewing device 26, which may be a TV camera, captures images in the bodily lumen, and the images can be electrically or optically transmitted through the scope portion 22 of the endoscope 12. The working channel 28 can extend through the scope portion 22 to the distal end portion 20 of the endoscope 12. The working channel 28 can be designed to accommodate various medical instruments.

Referring to FIGS. 1A-B, the sheath assembly 10 of the present invention comprises an elongate tubular body 30 that extends along a longitudinal axis LA located between a distal end 32 having a first distal end opening 34 and a proximal end 36 having a first proximal end opening 38. Although the body 30 is shown in FIGS. 1A-B as having a tubular shape, it will be appreciated that the body can have other shapes so that the sheath assembly 10 can readily conform to the outer surface of an endoscope 12. For example, the body 30 of the sheath assembly 10 can have a D-shaped or ovoid cross-sectional profile. The sheath assembly 10 can be made from one or a combination of materials that allows the sheath assembly to readily bend and flex along with the endoscope 12 during use. For example, all or only a portion of the sheath assembly 10 can be made from the same or different polymeric materials, which may be thermoplastic or thermoset. Such materials are known in the art and can include, for example, thermoplastic elastomers, such as styrenic block copolymers, polyolefin blends, elastomeric alloys, thermoplastic polyurethanes, thermoplastic copolyesters, and thermoplastic polyamides, as well as thermoset elastomers, such as silicones.

As shown in FIG. 3A, the tubular body 30 comprises first and second wall sections 40 and 42. The first wall section 40 extends radially about the longitudinal axis LA to define a scope lumen 44. Although not shown, the scope portion 22 of the endoscope 12 is receivable coaxially in the scope lumen 44 so that the distal end 32 of the body 30 is disposed adjacent the endoscope tip 14, and the proximal end 36 is disposed adjacent the handle portion 18 of the endoscope.

The scope lumen 44 of the sheath assembly 10 is form-fitting over an outer diameter (OD) of the scope portion 22, which requires minimal clearance between the OD and an inner diameter (ID) of the scope lumen. The outer surface of the scope portion 22 has a relatively high coefficient of friction. Placing the form-fitting sheath assembly 10, which is made of a relatively thin and flexible material, over the outer surface of the endoscope 12 can be difficult. To aid in installation and removal of the sheath assembly 10, a lubricant may be used. For example, a lubricant can be applied to the outer surface of the scope portion 22 of the endoscope 12. Alternatively, the ID of the sheath assembly 10 may be lightly lubricated (e.g., using USP Class VI/ISO 10993 materials) prior to mating with the endoscope 12 or during production. Applying a lubricant may be useful as it has been found that a light internal coating of lubricant makes it possible (with minimal effort) to place and remove the sheath assembly 10 over the endoscope 12. It will be appreciated that applying lubrication can also prevent the sheath assembly 10 from collapsing and sticking to itself when packaged.

The second wall section 42 of the body 30 extends radially about at least a portion of the first wall section 40. In one example of the present invention, the second wall section 42 can extend radially about less than the entire first wall section 40. Alternatively, the second wall section 42 can extend radially around the entire first wall section 40. The second wall section 42 defines an outer second wall diameter ($OD_s$) of about 6.5 mm. In one example of the present invention, the $OD_s$ does not exceed 6.5 mm. The second wall section 42 also extends longitudinally along the longitudinal axis LA between a second distal end opening 46 that is adjacent the first distal end opening 34, and a second proximal end opening (not shown) that is adjacent the first proximal end opening 38. The second proximal end opening is formed as an aperture through the second wall section 42. The first and second wall sections 40 and 42 define an integral suction lumen 50 therebetween that is connectable in fluid communication with a first source of negative pressure (not shown), such as a vacuum pump. The first and second distal end openings 34 and 46 are generally coterminous. The suction lumen 50 has a cross-sectional area that may be equal to or greater than the cross-sectional area of the scope lumen 44. Alternatively, the suction lumen 50 can have a cross-sectional area that is less than the cross-sectional area of the scope lumen 44. The sheath assembly 10 can have a single suction lumen 50, two suction lumens (FIG. 3B), three suction lumens (FIG. 3A), or even more suction lumens.

As shown in FIGS. 3A-B, the suction lumen 50 includes at least one rib member 52 for preventing collapse of the suction lumen when the first source of negative pressure is applied thereto. The at least one rib member 52 extends radially within the suction lumen 50 from a distal end 54 that is integral with one of the first and second wall sections 40 and 42 to a proximal end 56 that is disposed opposite the other one of the first and second wall sections. Depending upon the orientation of the distal end 54, the proximal end 56 is bearable on one of the first and second wall sections 40 and 42 to support the suction lumen 50 when the first source of negative pressure is applied. In the absence of negative pressure or suction within the suction lumen 50, the proximal end 56 of the at least one rib member 52 is free from contact with one of the first and second wall sections 40 and 42. The at least one rib member 52 also extends along at least a portion of the longitudinal axis LA. For example, the at least one rib member 52 can extend along the entire longitudinal axis LA. The at least one rib member 52 can have any suitable shape (e.g., finger-shaped, wedge-shaped, etc.).

Any number of rib members 52 can be disposed within the suction lumen 50. As shown in FIG. 3A, two rib members 52 are disposed within the suction lumen 50. Alternatively, as shown in FIG. 3B, the suction lumen 50 can include only one rib member 52 disposed therein. During application of negative pressure or suction within the suction lumen 50, the proximal end 56 of the at least one rib member 52 can contact a portion of the second wall section 42 (i.e., opposite the distal end 54 of the at least one rib member) and thereby prevent the suction lumen from collapsing. By forming the at least one rib member 52 such that the proximal end 56 is not permanently joined to the portion of the second wall section 42, the presence of the at least one rib member does not appreciably degrade the overall flexibility of the sheath assembly 10.

It will be appreciated that the sheath assembly 10 is sufficiently flexible such that it cannot significantly impede the ability to articulate the tip 14 of the endoscope 12. There may be concern that the thin walls and high flexibility of the sheath assembly 10 might make the suction lumen 50 prone to collapse. Advantageously, the sheath assembly 10 of the present invention can be designed with multiple suction lumens 50. In such a multi-lumen configuration, there may be a concern that the walls separating the suction lumens 50 might act like "I" beams and make the sheath assembly 10 too stiff. By incorporating a single, large suction lumen 50 having at least one rib member 52 (FIG. 3B), and more particularly two rib members within the suction lumen (FIG. 3A), collapse is prevented. Moreover, by de-coupling the rib members 52 at the point where they would otherwise attach to the outer surface of the endoscope 12, or the sheath body 30 itself, the rib members do not tend to act like "I" beams.

Figure 4A:
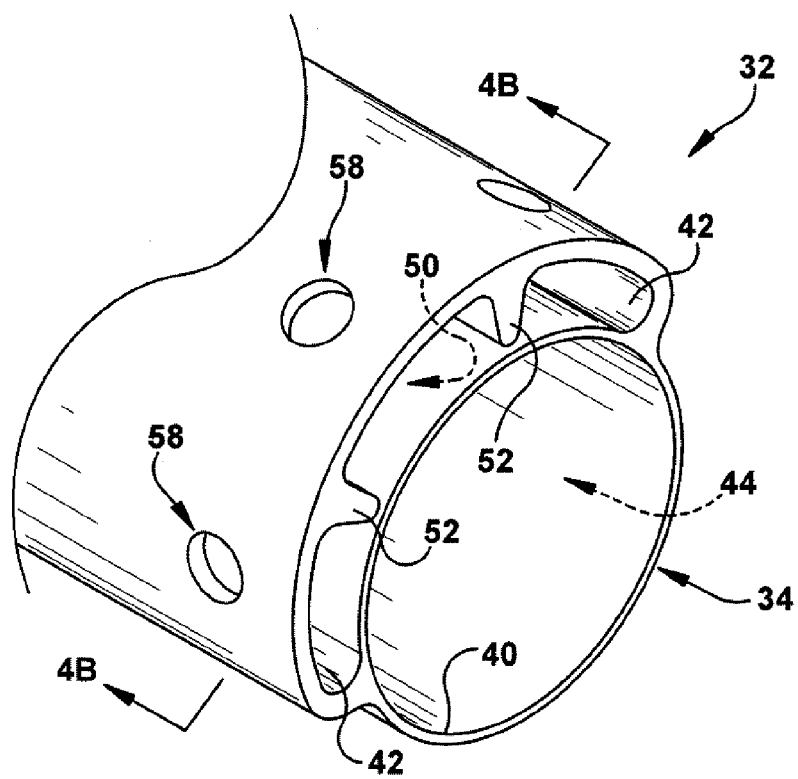
FIG. 4A is a schematic illustration showing a perspective view of another alternative configuration of the distal end in FIG. 3A.
Figure 4B:
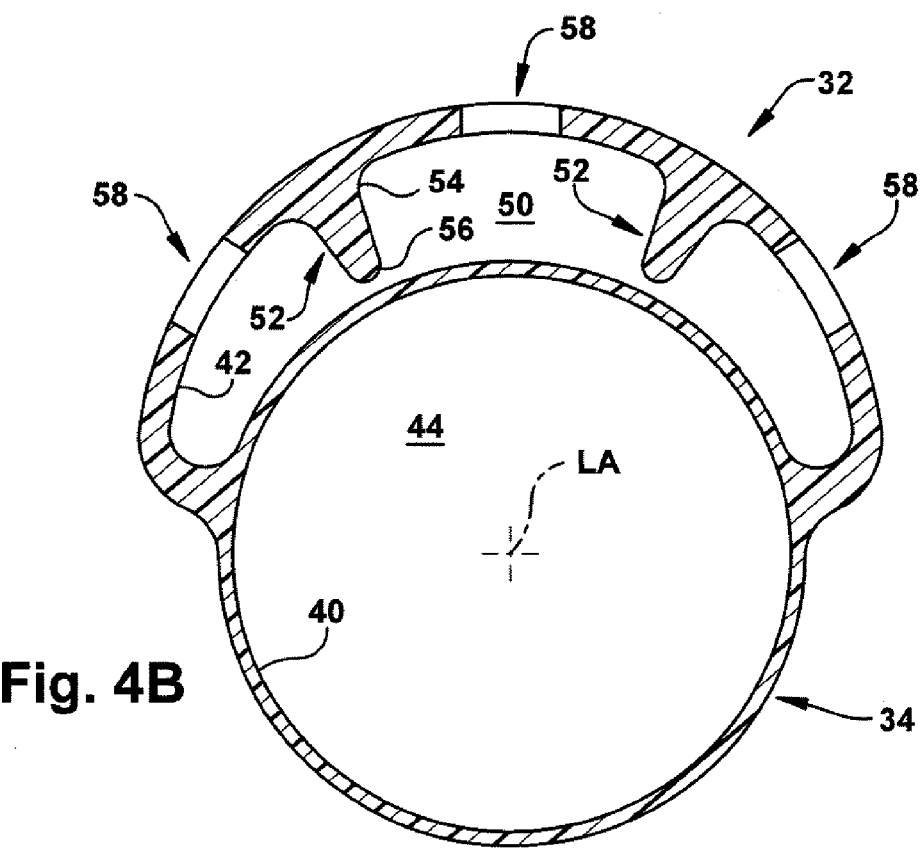
FIG. 4B is a cross-sectional view taken along Line 4B-4B in FIG. 4A.

Referring to FIGS. 4A-B, the distal end 32 of the sheath assembly 10 can optionally include at least one aperture 58. The at least one aperture 58 can extend through the second wall section 42 such that the suction lumen 50 is in fluid communication with the environment external to the sheath assembly 10. The at least one aperture 58 can facilitate suctioning by providing additional surface area through which bodily fluids can be aspirated into the suction lumen 50. Although only three apertures 58 are illustrated in FIGS. 4A-B, it will be appreciated that any number of apertures may be included about the distal end 32 of the sheath assembly 10. Additionally, it will be appreciated that the at least one aperture 58 can have a cross-sectional profile other than the circular cross-sectional profile shown in FIGS. 4A-B (e.g., square, ovoid, rectangular, etc.).

Another aspect of the present invention includes a plug 60 (FIGS. 5A-C) configured to mate with the first distal end opening 34 of the body 30 for closing the scope lumen 44. The plug 60 is mated with the first distal end opening 34. For example, the plug 60 can be inserted into the first distal end opening 34 (e.g., friction fit and/or RF welded thereto), integrally connected to the distal end 32 (e.g., by RF welding), or placed over the distal end 32 to cover the first distal end opening 34. The plug 60 can be secured to the distal end 32 of the body 30 by RF welding, for example. As described above, most endoscopes 12 include three fiber optic bundles, two of which are used for illumination purposes while the third is used for visualization purposes. When covering these optical bundles with a sheath, there is the potential for reflecting light back onto the visualization optic fiber bundle. The greater the distance between a cover and the fiber optic bundles, the closer to the center of the field of view the light will be reflected. To prevent or mitigate this occurrence, the plug 60 of the present invention includes a lens surface 62 through which light or other energy is transmissible to or from the endoscope tip 14. The plug 60, and in particular the lens surface 62, is configured such that any reflected light is only present in the peripheral field of view, thereby yielding superior optical quality. As described in more detail below, the plug 60 provides significant surface area to facilitate a robust bond with the first distal end opening 34, as well as an anti-traumatic surface on the distal end 32 of the sheath assembly 10.

The plug 60 is configured to have a cross-sectional design that essentially mirrors the cross-sectional design of the body 30. Generally, the plug 60 provides structural rigidity to the distal end 32 of the sheath assembly 10 during application of negative pressure or suction to the scope lumen 44 and/or the suction lumen 50. As shown in FIGS. 5A-C, the plug 60 comprises a first portion 64 that is integrally formed with a second portion 66, which is configured to snugly mate with the first distal end opening 34 of the body 30. The plug 60 includes a first wall section 68 that extends radially about a longitudinal axis LA' to partly define a cavity 70, which is further defined by the lens surface 62. The cavity 70 can be configured to receive the tip 14 of the endoscope 12. All or only a portion of the plug 60 is formed from a transparent plastic material. For example, the lens surface 62 is formed from a transparent plastic material through which light or other energy is transmissible to or from the endoscope tip 14. To further reduce any reflected light, a biocompatible anti-reflective coating (not shown) can be added to the lens surface 62.

The plug 60 further includes a second wall section 72 that extends radially about at least a portion of the first wall section 68, and longitudinally along the longitudinal axis LA' between a distal opening 74 and a proximal opening 76. Each of the second wall section 72, the proximal opening 76, and the distal opening 74 collectively define a suction opening 78 that is disposed in registration with the second distal end opening 46 of the body 30. A portion of the second wall section 72 forms a wall 80 that extends longitudinally between the distal and proximal openings 74 and 76. The wall 80 is longitudinally aligned with a rib member 52 comprising the suction lumen 50. As shown in FIG. 5B, the plug 60 can include two walls 80 and three suction openings 78. It will be appreciated that the plug 60 can include any number of walls 80 and suction openings 78, depending upon the number of rib members 52 comprising the suction lumen 50.

Figure 6:
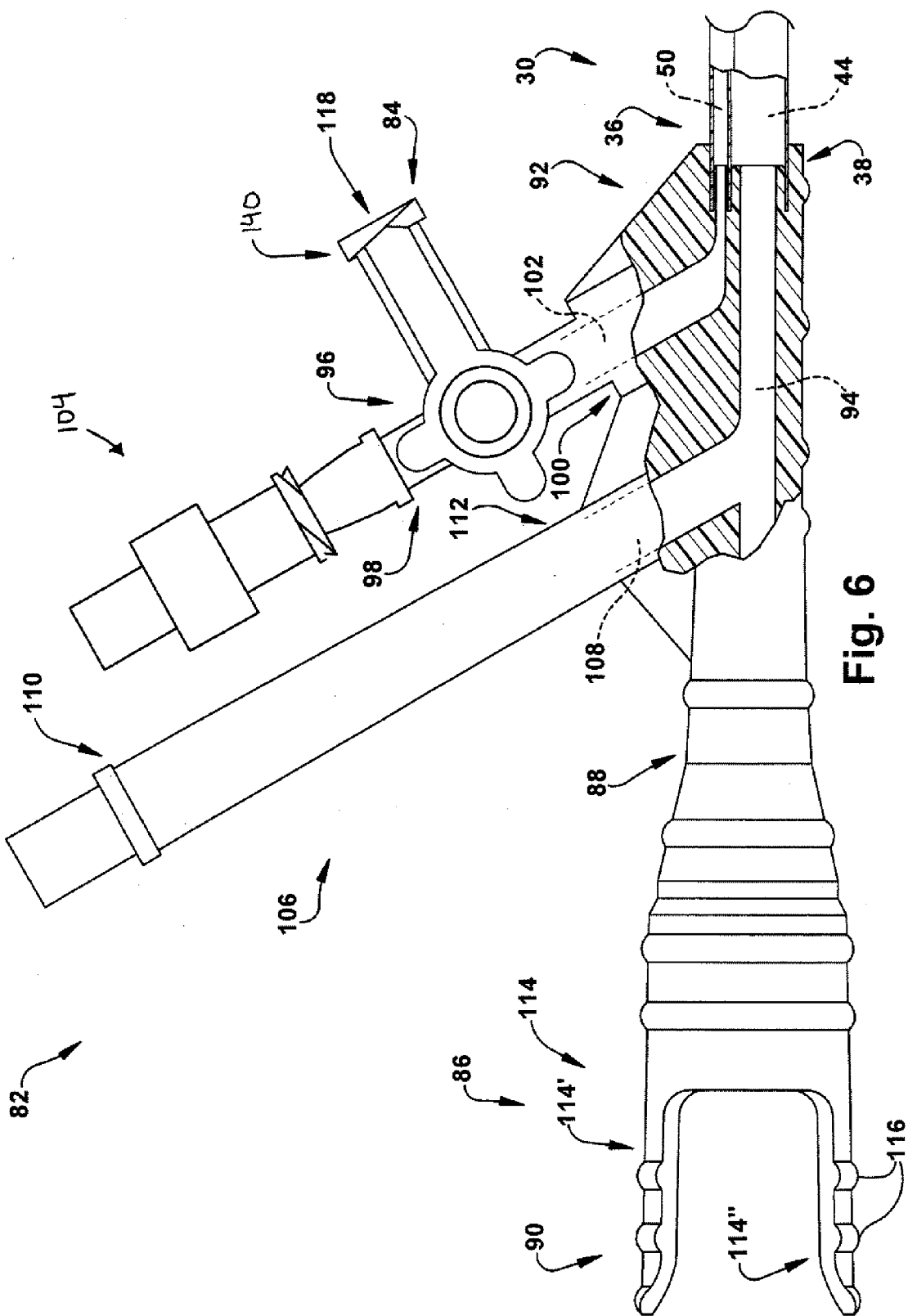
FIG. 6 is a schematic illustration showing a partial cutaway of the connector in FIG. 1B.

Another aspect of the present invention includes a connector 82 (FIG. 6). As described in more detail below, the connector 82 provides a non-balloon-based method for visually determining whether the sheath assembly 10 has been damaged during a procedure. The connector 82 extends longitudinally between a forward end portion 84, which coaxially surrounds the first and second proximal end openings 38, and a rearward end portion 86 configured to fit onto the handle portion 18 of the endoscope 12. The connector 82 includes a main body portion 88 that extends between a proximal end 90 and a distal end 92. The distal end 92 is mated to the proximal end 36 of the body 30 using RF welding, for example. A first lumen 94, which extends between the proximal and distal ends 90 and 92 of the main body portion 88, is in fluid communication with the scope lumen 44. Although the connector 82 has a generally cylindrical configuration, it will be appreciated that the connector can have any configuration adapted to snugly mate with the handle portion 18 of the endoscope 12. The connector 82 can be formed from a flexible and/or elastic material, such as one or a combination of molded polymers.

The forward end portion 84 includes a tubular, elongate suction port 96 that opens into fluid communication with the suction lumen 50 of the body 30. As shown in FIG. 6, the suction port 96 is integrally formed with the main body portion 88 of the connector 82. The suction port 96 includes oppositely disposed first and second ends 98 and 100 and a second lumen 102 that extends between the first and second ends. The second lumen 102 is in fluid communication with the suction lumen 50. The second end 100 is integrally connected to the distal end 92 of the main body portion 88. The first end 98 of the suction port 96 is adapted to receive a hand valve 122 (FIG. 8), which can be manually controlled by a clinician during application of negative pressure or suction by the first vacuum source. Although the suction port 96 (FIG. 6) has a generally cylindrical or tubular configuration, it will be appreciated that the suction port can have any desired configuration. It will also be appreciated that the suction port 96 can include a three-way stopcock 140 operably secured thereto. As shown in FIG. 6, a one-way duck bill valve 104 can be securely mated to the stopcock 140. The duck bill valve 104 can prevent fluids aspirated into the suction lumen 50 from running back into the patient when suction is removed.

Referring to FIGS. 1A-B, a plug assembly 142 is connected to the duck bill valve 104 via a length of tubing 144. The plug assembly comprises a hand valve 122 integrally formed with a plug member 146, which is configured to mate with an integral valve port 136 (FIGS. 8-9) of an endoscope 12. The plug member 146 has a generally cylindrical shape and extends transverse, or substantially transverse to, the opening 118 of the hand valve 122. More particularly, the plug member 146 includes a first free end portion 148 oppositely disposed from a secured second end portion 150. The first free end portion 148 is adapted to be inserted into the integral valve port 136 and thereby disable the integral valve (not shown) of the endoscope 12. As described below, disabling the integral valve allows an endoscope user to operate the endoscope 12 when the sheath assembly 10 is disposed thereon. The secured second end portion includes a base 152 that is securely connected to the hand valve 122. The base 152 can be integrally formed from a portion of the hand valve 122 or, alternatively, securely connected thereto via an adhesive, RF welding, or other known attachment means. All or only a part of the plug member 146 can be made of a rigid and/or semi-rigid material, such as a metal or plastic.

Application of the plug assembly 142 to the endoscope 12 is shown in FIGS. 8-9. The hand valve 122 of the plug assembly 142 can first be connected to a length of tubing 144, which is connected to the one-way duck bill valve 104. The hand valve 122 can then be further connected to the first source of negative pressure. The plug assembly 142 can then be positioned about the integral valve port 136 of the endoscope 12 as shown in FIG. 8. Next, the plug member 146 is inserted into the integral valve port 136, which disables the integral valve of the endoscope 12. Once the plug member 146 is securely inserted into the integral valve port 136, negative pressure or suction can be applied to a suction line (not shown) (e.g., via hospital house suction) connecting the hand valve 122 to the first source of negative pressure. In turn, a vacuum is constantly present so that actuation of the valve 122 by a clinician introduces a vacuum into the suction lumen 50 of the endoscope 12.

The rearward end portion 86 of the connector 82 includes a tubular, elongate lumen port 106 that opens into fluid communication with the scope lumen 44 of the body 30. The lumen port 106 is connectable in fluid communication with a second source of negative pressure (not shown) for evacuating the scope lumen 44. The lumen port 106 is collapsibly responsive to such evacuation as an indication of the fluid-tight integrity of the scope lumen 44 when the sheath assembly 10 is used in service. The lumen port 106 is located proximate the suction port 96 and includes a third lumen 108 extending between oppositely disposed first and second ends 110 and 112. The second end 112 of the lumen port 106 is integrally connected to the main body portion 88 such that the first and third lumens 94 and 108 are in fluid communication with one another. It will be appreciated that the lumen port 106 can include other mechanisms to indicate drawing of a vacuum therethrough. For example, the wall comprising the lumen port 106 can be made of a colored and mostly translucent material that changes to a darker color when the third lumen 108 collapses, thereby visually indicating drawing of a vacuum through the lumen port. It will also be appreciated that the lumen port 106 can include a check valve 138 operably disposed therein.

The rearward end portion 86 of the connector 82 additionally includes at least one flap 114 that is disposable on the handle portion 18 of the endoscope 12. The flap 114 can be liftable manually from the handle portion 18 to break the seal between the connector 82 and the handle portion when the scope lumen 44 is evacuated. In one example of the present invention, the connector 82 can include first and second flaps 114' and 114" that are integrally connected to, and extend from, the distal end 92 of the main body portion 88. Each of the flaps 114' and 114" has a generally bullet-shaped configuration; however, it will be appreciated that other shapes or configurations may be used. Additionally, it will be appreciated that the connector 82 can include one, three, four or more flaps 114. Each of the flaps 114 can also include at least one ridge 116 to facilitate manual manipulation of the flaps and the connector 82.

Figure 7:
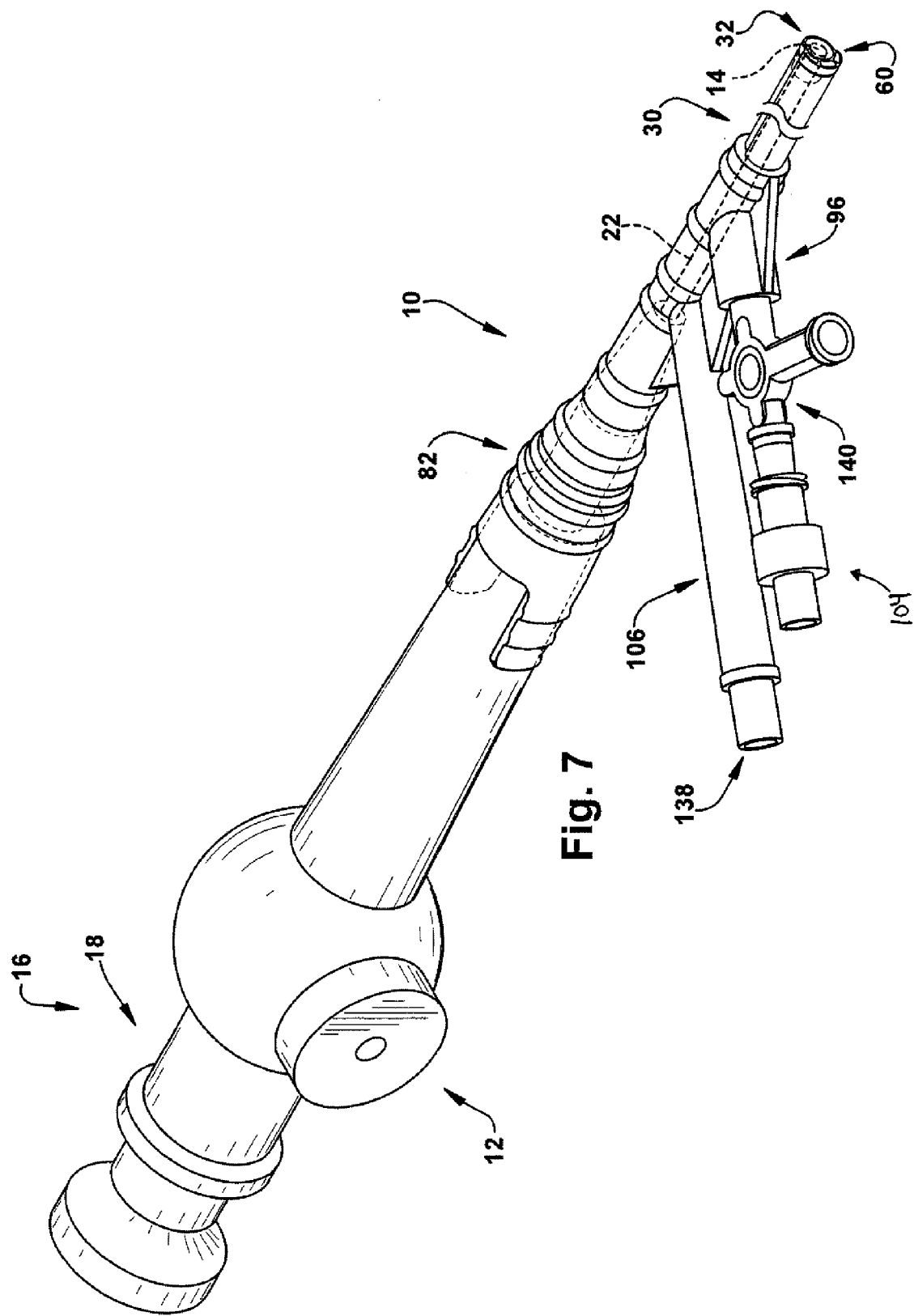
FIG. 7 is a schematic illustration showing a perspective view of the sheath assembly in FIGS. 1A-B mated with the handle portion of an endoscope.

Since placement of the sheath assembly 10 over the endoscope 12 disables the internal suction lumen of the endoscope, use of the hand piece valve port (not shown) is no longer viable. To provide external suction capability, a hand valve 122 (FIG. 8) can be mated with the suction port 96 after applying the connector 82 to the endoscope 12 (FIG. 7). The hand valve 122 (FIG. 8) is shaped like a shallow cradle that conforms to the curve of an index finger. The cradle has an opening 118 in the center so that when a finger is placed over it, a vacuum, which is drawn through the second lumen 102, is increased. Since the suction port 96 may extend beyond (e.g., about six inches) the main body portion 88 of the connector 82, a clinician can position the hand valve 122 near the disabled hand valve of the endoscope 12.

Another aspect of the present invention includes a clip and valve assembly 120 (FIGS. 10-11) for mounting on the handle portion 18 of an endoscope 12. As shown in FIG. 10, the clip and valve assembly 120, which may be unitary or formed of separate parts, comprises a valve 122 (e.g., a hand suction valve) and a clip 124 configured to hold the valve. The clip 124 has a generally U-shaped configuration and includes first and second leg members 126 and 128 configured to mate with the handle portion 18 of an endoscope 12. The clip 124 also includes a connecting section 130 that is disposed between, and integrally formed with, the first and second leg members 126 and 128. As shown in FIG. 10, the connecting section 130 includes oppositely disposed first and second arm members 132 and 134 that are capable of holding (e.g., by friction or tension fitting) the valve 122. All or only a part of the clip 124 can be made of a rigid and/or semi-rigid material, such as a metal or plastic. In an alternative construction, the clip 24 may have a generally ring-shaped configuration.

In use, the clip and valve assembly 120 may be positioned in an ergonomic location, such as immediately adjacent the integral valve port 136 of the endoscope 12, or elsewhere on the endoscope as may be convenient for operation by the physician or clinician for single-handed control of articulation and suctioning by the endoscope. In this manner, the clip and valve assembly 120 is locked into an ergonomic position and ready for use. To apply suction, a suction line (not shown) can be attached to the valve 122 of the clip and valve assembly 120. Upon application of negative pressure or suction to the suction line (e.g., via hospital house suction), a vacuum is constantly present so that actuation of the valve 122 by a clinician introduces a vacuum into the suction lumen 50 of the endoscope 12. During use, the endoscope 12 can be held by the clinician like a policeman holds a flash light (e.g., exiting the hand opposite the thumb). In this manner, the endoscope articulation control lever (not shown in detail) is easily controlled by the thumb while the index finger is on top of the handle portion 18.

Another aspect of the present invention includes a method for determining whether the integrity of the sheath assembly 10 has been compromised. As discussed above, the connector 82 of the sheath assembly 10 includes a leak detection mechanism (i.e., the lumen port 106) for indicating when a fluid-tight seal has been compromised during application of negative pressure or suction to the scope lumen 44. The method described below provides an additional mechanism for determining if the integrity of the sheath assembly 10 has been compromised by, for example, a micro-sized tear or puncture (e.g., about 5 microns). Detection of such micro-sized tears or punctures is important since some bacteria may be able to infiltrate the scope lumen 44 through such tears or punctures, yet such tears or punctures are difficult to detect due to their minute size. Advantageously, the method of the present invention can be used to rapidly detect a minute leak (or leaks) in the sheath assembly 10 before and/or after use of the sheath assembly.

In one example of the method, a fluid-based leak test can be performed before and/or after use of the sheath assembly 10 to determine whether the integrity of the sheath assembly has been compromised. To evaluate the integrity of the sheath assembly 10 prior to use, the packaging (not shown) used to store the sheath assembly can be used as a leak detection mechanism. The packaging can comprise, for example, an elongate, transparent splittable pouch (not shown) having a proximal end for inserting the sheath assembly 10 therein, and a closed distal end. The splittable pouch includes a vessel disposed therein configured to hold a volume of fluid (e.g., water or saline). The vessel can comprise an elongate, tubular member having a closed distal end and a length sufficient to enclose the entire body 30 of the sheath assembly 10. The vessel can be comprised of a lightweight plastic or other similar material capable of holding a fluid volume.

Prior to using the sheath assembly 10, the splittable sheath can be opened by separating opposing portions located at the proximal end thereof. A volume of fluid (e.g., about 35 cc) can then be poured into the pouch so that the vessel is sufficiently filled to envelop the body 30 of the sheath assembly 10. Next, a sealing mechanism located at the proximal end of the pouch can be used to provide a water-tight fit of the body 30 within the pouch. A source of air (or other gas, such as helium) can then be used to pressurize the scope lumen 44. For example, a syringe (not shown) containing a volume of air can be operably attached to the lumen port 106 (e.g., via the check valve 138 or a stopcock) and then depressed to pressurize the scope lumen 44. Once the scope lumen 44 is pressurized, a user can monitor the pouch for evidence of bubble formation (e.g., on the surface of the body 30). The presence of at least one bubble emanating from the body 30 indicates a leak in a portion of the sheath assembly 10.

To evaluate the integrity of the sheath assembly 10 after use, the sheathed endoscope 12 can be re-inserted into the pouch. As described above, a source of air can then be used to pressurize the scope lumen 44. For example, a syringe containing a volume of air can be operably attached to the lumen port 106 (e.g., via the check valve 138 or a stopcock) and then depressed to pressurize the scope lumen 44. A user can then monitor the container for evidence of bubble formation (e.g., on the surface of the body 30). The presence of at least one bubble emanating from the body 30 indicates a leak in a portion of the sheath assembly 10.

One skilled in the art will appreciate variations in the fluid-based leak detection system of the present invention. For example, instead of infusing air into the scope lumen 44, a volume of a colored fluid, such as a non-toxic dye can be infused into the scope lumen. If the integrity of the sheath assembly 10 is compromised, the colored fluid will leak into the surrounding water (or other fluid), thereby indicating a puncture or tear in the sheath assembly.

An alternative leak detection system can include a litmus test that may be performed before and/or after a procedure. To do so, a coating can first be applied to the inner surface of the body 30. The coating can change colors upon contact with a particular fluid or solution. For example, the coating can be capable of changing color upon exposure to an alkaline solution. Post procedure, for example, a clinician or technician can submerge the sheathed endoscope 12 into the alkaline solution with the vacuum still applied to the sheath assembly 10. If there is a defect or compromise in the body of the sheath assembly 10, the solution will have a pathway to reach the coating. The clinician or technician can then remove the sheathed endoscope 12 from the solution, remove the sheath assembly 10 from the endoscope, and inspect the sheath assembly for any area(s) displaying a color change.

From the above description of the invention, those skilled in the art will perceive improvements, changes and modifications. For example, one skilled in the art will appreciate that other sheath assembly 10 configurations are possible, such as a tube-in-tube configuration (not shown). Such improvements, changes, and modifications are within the skill of the art and are intended to be covered by the appended claims.

Having described the invention, the following is claimed:

1. A sheath assembly for an endoscope, the endoscope having a handle portion and an elongate scope portion extending from the handle portion to a tip, the sheath assembly comprising:
   an elongate tubular body extending along a longitudinal axis between a first distal end opening located at a distal end thereof and a first proximal end opening located at a proximal end thereof, the body comprising:
      a first wall section extending radially about the longitudinal axis to define a scope lumen, the scope portion of the endoscope being receivable coaxially in the scope lumen with the distal end of the body being disposed adjacent the endoscope tip and the proximal end of the body being disposed adjacent the handle portion of the endoscope; and
      a second wall section extending radially about at least a portion of the first wall section and longitudinally along the longitudinal axis between a second distal end opening adjacent the first distal end opening and a second proximal end opening adjacent the first proximal end opening, the first and the second wall sections defining an integral suction lumen therebetween connectable in fluid communication with a first source of negative pressure; and
   a plug mated with the first distal end opening of the body for closing the scope lumen, the plug having a lens surface through which light or other energy is transmissible to or from the endoscope tip, the plug further have at least one suction opening therein disposed in co-registration with the second distal end opening of the body.

2. The sheath assembly of claim 1, wherein the first and second distal end openings are coterminous.

3. The sheath assembly of claim 1, wherein at least one aperture extends through the second wall section such that the suction lumen is in fluid communication with an environment external to the sheath assembly.

4. The sheath assembly of claim 1, wherein the plug has a cross-sectional profile that mirrors a cross-sectional profile of the elongate tubular body.

5. The sheath assembly of claim 1, wherein the lens surface of the plug is formed from a transparent plastic material.

6. A sheath assembly for an endoscope, the endoscope having a handle portion and an elongate scope portion extending from the handle portion to a tip, the sheath assembly comprising:
   an elongate tubular body extending along a longitudinal axis between a first distal end opening located at a distal end thereof and a first proximal end opening located at a proximal end thereof, the body comprising:
      a first wall section extending radially about the longitudinal axis to define a scope lumen, the scope portion of the endoscope being receivable coaxially in the scope lumen with the distal end of the body being disposed adjacent the endoscope tip and the proximal end of the body being disposed adjacent the handle portion of the endoscope;
      a second wall section extending radially about at least a portion of the first wall section and longitudinally along the longitudinal axis between a second distal end opening adjacent the first distal end opening and a second proximal end opening adjacent the first proximal end opening, the first and the second wall sections defining an integral suction lumen therebetween connectable in fluid communication with a first source of negative pressure; and
   a plug mated with the first distal end opening of the body for closing the scope lumen, the plug having a lens surface through which light or other energy is transmissible to or from the endoscope tip;
   wherein the body further comprises at least one rib member extending radially within the suction lumen from a distal end integral with one of the first and the second wall sections to a proximal end disposed opposite the other one of the first and the second wall sections and being bearable thereon to support the suction lumen when the first source of negative pressure is applied, wherein the proximal end of the at least one rib member is free from contact with one of the first and second wall sections in the absence of negative pressure within the suction lumen.

7. The sheath assembly of claim 6, wherein the plug has a cross-sectional profile that mirrors a cross-sectional profile of the elongate tubular body.

8. The sheath assembly of claim 6, wherein at least one aperture extends through the second wall section such that the suction lumen is in fluid communication with an environment external to the sheath assembly.

9. The sheath assembly of claim 6, wherein the lens surface of the plug is formed from a transparent plastic material.

10. A sheath assembly for an endoscope, the endoscope having a handle portion and an elongate scope portion extending from the handle portion to a tip, the sheath assembly comprising:
- an elongate tubular body extending along a longitudinal axis between a first distal end opening located at a distal end thereof and a first proximal end opening located at a proximal end thereof, the body comprising:
  - a first wall section extending radially about the longitudinal axis to define a scope lumen, the scope portion of the endoscope being receivable coaxially in the scope lumen with the distal end of the body being disposed adjacent the endoscope tip and the proximal end of the body being disposed adjacent the handle portion of the endoscope;
  - a second wall section extending radially about at least a portion of the first wall section and longitudinally along the longitudinal axis between a second distal end opening adjacent the first distal end opening and a second proximal end opening adjacent the first proximal end opening, the first and the second wall sections defining an integral suction lumen therebetween connectable in fluid communication with a first source of negative pressure; and
- a plug mated with the first distal end opening of the body for closing the scope lumen, the plug having a lens surface through which light or other energy is transmissible to or from the endoscope tip; and
- a leak-detection mechanism coupled to the body and being configured to provide an indication of the integrity of the sheath assembly before and/or after use.

11. The sheath assembly of claim 10, wherein the leak-detection mechanism is non-balloon-based.

12. The sheath assembly of claim 10, wherein the leak-detection mechanism further comprises:
- a connector extending longitudinally between a forward end portion that coaxially surrounds the first and second proximal end openings and a rearward end portion configured to fit onto the handle portion of the endoscope, the rearward end portion of the connector including an elongate lumen port having a third lumen that opens into fluid communication with the scope lumen of the body, the lumen port being connectable in fluid communication with a second source of negative pressure for evacuating the scope lumen;
- wherein a wall comprising the lumen port is made of a material having a color that changes upon collapse of the third lumen to visually indicate drawing of vacuum through the lumen port.

13. The sheath assembly of claim 10, wherein at least one aperture extends through the second wall section such that the suction lumen is in fluid communication with an environment external to the sheath assembly.

14. The sheath assembly of claim 10, wherein the first and second distal end openings are coterminous.

* * * * *

UNITED STATES PATENT AND TRADEMARK OFFICE
CERTIFICATE OF CORRECTION

PATENT NO. : 9,433,344 B2
APPLICATION NO. : 14/450562
DATED : September 6, 2016
INVENTOR(S) : Rafi Avitsian et al.

Page 1 of 1

It is certified that error appears in the above-identified patent and that said Letters Patent is hereby corrected as shown below:

In the claims,

Column 12, Line 5 reads "have at least" should read --having at least--

Signed and Sealed this
Twenty-second Day of November, 2016

Michelle K. Lee
*Director of the United States Patent and Trademark Office*